United States Patent [19]

Debernardis et al.

[11] Patent Number: 4,500,543
[45] Date of Patent: Feb. 19, 1985

[54] SUBSTITUTED 1-AMINOMETHYL-PHTHALANS

[75] Inventors: John F. Debernardis, Lake Villa; David L. Arendsen, Libertyville, both of Ill.

[73] Assignee: Abbott Laboratories, North Chicago, Ill.

[21] Appl. No.: 383,632

[22] Filed: Jun. 1, 1982

[51] Int. Cl.³ ............... A61K 31/34; C07D 307/78
[52] U.S. Cl. ........................... 514/469; 549/304; 549/459; 549/467
[58] Field of Search ................... 549/467; 424/285

[56] References Cited

U.S. PATENT DOCUMENTS

| 3,200,132 | 8/1965 | Werner | 549/467 |
| 3,467,675 | 9/1969 | Petersen et al. | 549/467 |
| 3,513,239 | 5/1970 | Wiley et al. | 549/467 |
| 3,859,279 | 1/1975 | Fothergill et al. | 549/467 |

FOREIGN PATENT DOCUMENTS

| 1148214 | 4/1969 | United Kingdom | 549/467 |
| 1200892 | 8/1970 | United Kingdom | 549/467 |

Primary Examiner—Ethel G. Love
Attorney, Agent, or Firm—Steven F. Weinstock; Martin L. Katz; Dennis K. Shelton

[57] ABSTRACT

Disclosed herein are 1-aminomethyl-phthalans represented by the formula

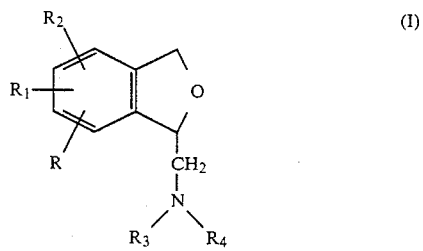

(I)

wherein R, $R_1$, and $R_2$ are independently selected from hydrogen, hydroxy, loweralkoxy of 1 to 3 carbon atoms, loweralkenyloxy of 1 to 3 carbon atoms, thiomethyl, halo, or

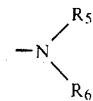

wherein $R_5$ and $R_6$ are independently selected from hydrogen, loweracyl of 1 to 4 carbon atoms or sulfonyl of the formula

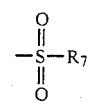

wherein $R_7$ is loweralkyl of 1 to 4 carbon atoms; or R and $R_1$, or $R_1$ and $R_2$ can be taken together to form a methylenedioxy or ethylenedioxy bridge; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

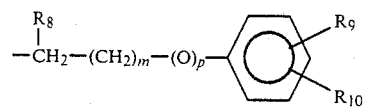

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo, or $R_9$ and $R_{10}$ can be taken together to form a methylenedioxy or ethylenedioxy bridge; or 1,4-benzodioxan of the formula

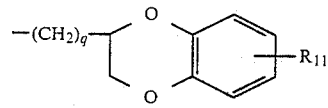

wherein q is 1, 2 or 3, and $R_{11}$ is hydrogen, methoxy, or halo; or $R_3$ and $R_4$ can be taken together to form a piperazino, piperidino or morpholino moiety; and the pharmaceutically acceptable salts thereof. Also disclosed are pharmaceutical compositions comprising compounds of formula (I) and a pharmaceutically acceptable carrier or diluent.

7 Claims, No Drawings

SUBSTITUTED 1-AMINOMETHYL-PHTHALANS

BACKGROUND AND SUMMARY OF THE INVENTION

This invention relates to novel phthalans, and more particularly to substituted 1-aminomethyl-phthalans useful in the treatment of hypertension.

The adrenergic nervous system plays a major role in the innervation of heart, blood vessel and smooth muscle tissue. Agents capable of interacting with receptor sites within the adrenergic nervous system can result in a variety of physiological responses, including vasoconstriction, vasodilation, and increased or decreased heart rate (chronotropic), contractility (inotropic) and metabolic activity. In the past, various adrenergic agents have been employed to affect these and other physiological responses. However, it is highly desirable to obtain new adrenergic agents which demonstrate a high degree of specificty for differing receptor types within the adrenergic nervous system in order to obtain a desired physiological response separate from other possible, and perhaps less desirable, responses of the system. This property has been lacking from most previously employed adrenergic agents. Thus, the search continues for new and improved adrenergic agents capable of selective interaction with adrenergic receptor sites.

It has now been determined that a new class of compounds, the substituted 1-aminomethyl-phthalans, as herein defined, demonstrate an ability to interact specifically with various adrenergic receptor types and are useful as therapeutic agents in the treatment of hypertension.

DESCRIPTION OF ILLUSTRATIVE EMBODIMENTS

The present invention provides 1-aminomethylphthalans represented by the formula I:

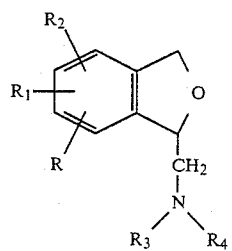
(I)

wherein R, $R_1$, and $R_2$ are independently selected from hydrogen, hydroxy, loweralkoxy of 1-3 carbon atoms, loweralkenyloxy of 1-3 carbon atoms, thiomethyl, halo, or

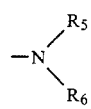

wherein $R_5$ and $R_6$ are independently selected from hydrogen, loweracyl of 1 to 4 carbon atoms or sulfonyl of the formula

wherein $R_7$ is loweralkyl of 1 to 4 carbon atoms; or R and $R_1$, or $R_1$ and $R_2$ can be taken together to form a methylenedioxy or ethylenedioxy bridge; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

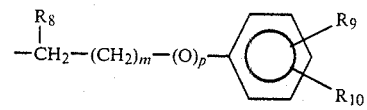

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo, or $R_9$ and $R_{10}$ can be taken together to form a methylenedioxy or ethylenedioxy bridge; or 1,4-benzodioxan of the formula

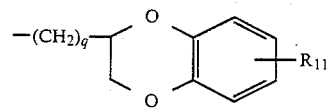

wherein q is 1, 2 or 3, and $R_{11}$ is hydrogen, methoxy, or halo; or $R_3$ and $R_4$ can be taken together to form a piperazino, piperidino or morpholino moiety; and the pharmaceutically acceptable salts thereof.

In a presently particularly preferred embodiment of the invention, the compounds of Formula I are 1-(substituted or unsubstituted) aminomethyl-4,5-dihydroxyphthalans, e.g., 1-aminomethyl-4,5-dihydroxy-phthalan, 1-dimethylaminomethyl-4,5-dihydroxy-phthalan, 1-isopropylaminomethyl-4,5-dihydroxy-phthalan, 1-di-n-propyl-aminomethyl-4,5-dihydroxy-phthalan, and the like.

As used herein, the term "loweralkyl of 1 to 4 carbon atoms" means straight or branched chain saturated hydrocarbon radicals, such as methyl, ethyl, n-propyl, iso-propyl, n-butyl, s-butyl, and t-butyl. The term additionally includes halo-substituted loweralkyl groups such as, for example, trifluoromethyl, 2-trichloroethyl, and the like.

As used herein, the term "halo" means chloro, bromo, fluoro and iodo.

As used herein, the term "loweracyl" means an acyl group represented by the formula

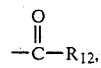

wherein $R_{12}$ is loweralkyl as herein defined. Illustrative acyl groups useful in the practice of the invention are acetyl, n-propionyl, iso-propionyl, n-butyryl, s-butyryl, t-butyryl, and the like.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per-N-salts.

The 1-aminomethyl-4,5-methylene dioxy and 4,5-dihydroxy compounds of formula I may be obtained according to the following reaction scheme I:

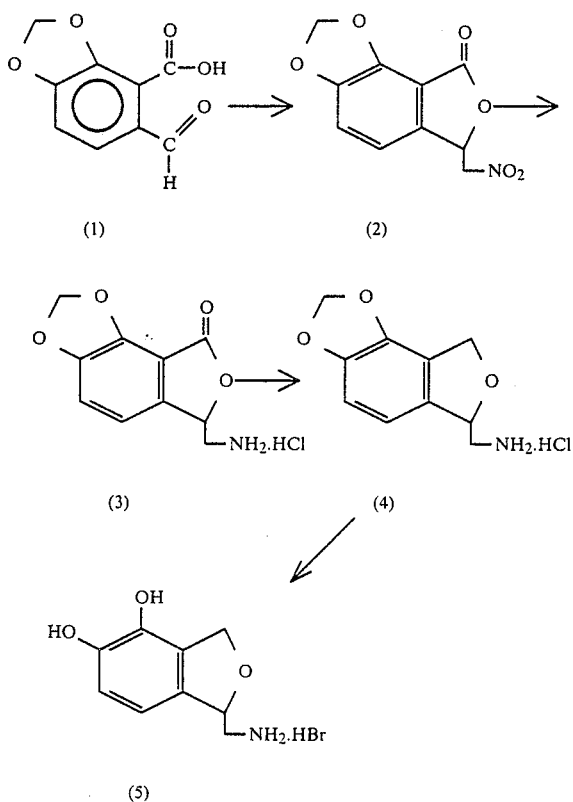

In accordance with reaction scheme I, 2,3-methylenedioxy-6-formyl-benzoic acid (1) is reacted with nitromethane in an aqueous solution under alkaline conditions, and the reaction mixture is acidified, such as with a mineral acid, e.g., hydrochloric acid, to obtain 1-nitromethyl-4,5-methylenedioxy-phthalide (2). Catalytic reduction of the 1-nitromethyl intermediate (2), such as over a 20% palladium-on-carbon catalyst in methanolic hydrochloric acid, results in the acid addition salt of 1-aminomethyl-4,5-methylenedioxy-phthalide (3). The compound 1-aminomethyl-4,5-methylenedioxy-phthalide is heated to reflux with diborane in tetrahydrofuran (THF), and then treated with methanolic hydrochloric acid to obtain 1-aminomethyl-4,5-methylenedioxy-phthalan hydrochloride (4). If desired, 1-aminomethyl-4,5-methylenedioxy-phthalan hydrochloride (4) may be converted to the corresponding 4,5-dihydroxy compound by suspension in methylene chloride and reaction with boron tribromide at a reduced temperature, such as −78° C., followed by decomposition of excess boron tribromide with methanol.

In a similar manner, the 1-aminomethyl-4,5-dialkoxy compounds of formula I may be obtained by substituting a 2,3-dialkoxy-6-formyl-benzoic acid for the 2,3-methylenedioxy-6-formyl-benzoic acid (1) of the foregoing reaction scheme I.

The 1-aminomethyl compounds of formula I which are disubstituted at the 5- and 6- positions, may be obtained according to the following reaction scheme II, wherein A represents loweralkyl:

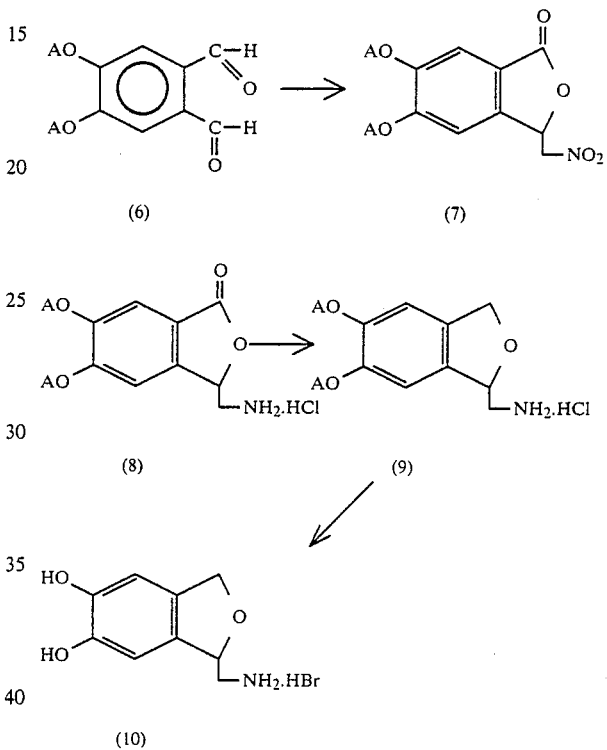

According to reaction scheme II, a 4,5-dialkoxy-1,2-benzenediformaldehyde compound (6) is reacted with nitromethane as heretofore described in connection with reaction scheme I to obtain the corresponding 1-nitromethyl-5,6-dialkoxy-phthalide compound (7). The nitromethyl phthalide is subjected to catalytic hydrogenation, such as over a 20% palladium-on-carbon catalyst in methanolic hydrogen chloride, resulting in 1-aminomethyl-5,6-dialkoxy-phthalide as the acid addition salt (8). The latter is reacted with diborane in THF as heretofore described to obtain the corresponding 1-aminomethyl-5,6-dialkoxy-phthalan (9), which may, if desired, be dealkylated with boron tribromide in methylene dichloride at reduced temperature to yield 1-aminomethyl-5,6-dihydroxy-phthalan hydrobromide (10).

The 1-aminomethyl compounds of formula I which are disubstituted at the 4- and 6-positions may be obtained according to the following reaction scheme III, wherein A represents loweralkyl:

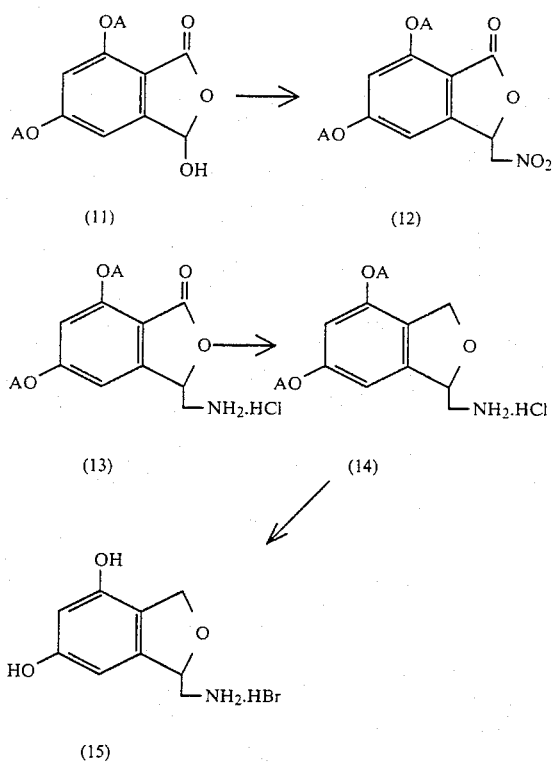

As set forth in reaction scheme III, a 3-hydroxy-5,7-dialkoxy-phthalide is reacted with nitromethane as heretofore described in connection with reaction schemes I and II to obtain the corresponding 1-nitromethyl-4,6-dialkoxy-phthalide (12). The nitromethyl phthalide (12) is subjected to catalytic hydrogenation, such as over a 20% palladium-on-carbon catalyst in methanolic hydrochloric acid, resulting in the acid addition salt of 1-aminomethyl-4,6-dialkoxy-phthalide (13), which is reacted with diborane in THF, as heretofore described in connection with reaction scheme I and II, to obtain the acid addition salt of the 1-aminomethyl-4,6-dialkoxy-phthalan (14). If desired, the dialkoxy compound (14) may be dealkylated by treatment with boron tribromide in methylene dichloride at reduced temperature to obtain 1-aminomethyl-4,6-dihydroxy-phthalan HBr (15). In addition, the 1-aminomethyl compounds of formula I which are monosubstituted at the 4-, 5- or 6-positions may be obtained according to reaction scheme III by replacing the 3-hydroxy-5,7-dialkoxy-phthalide (11) starting material in reaction scheme III with a 3-hydroxy-5-alkoxy phthalide, a 3-hydroxy-6-alkoxy-phthalide or a 3-hydroxy-7-alkoxy-phthalide.

Alternatively, the 1-aminomethyl compounds of formula I may be obtained by reacting a known phthalide compound of the formula

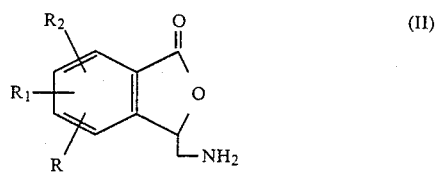

where R, $R_1$, and $R_2$ are as herein defined in connection with formula I, with diborane in THF at reflux under a nitrogen atmosphere.

The N-alkylated compounds of the invention are obtained by reacting a 1-aminomethyl-phthalide (II) with an aldehyde or ketone in the presence of sodium acetate and methanol, and then reducing the N-alkylated phthalamide to the corresponding phthalan as heretofore described. For example, a 1-aminomethyl-phthalide is reacted with formaldehyde to obtain a 1-(N,N-dimethyl)-aminomethyl-phthalide; with acetaldehyde to obtain a 1-(N-ethyl)aminomethyl-phthalide; with acetone to obtain a 1-(N-isopropyl)aminomethyl-phthalide; etc.; which may then be reduced to the corresponding phthalan compound.

In addition to the foregoing, the compounds of the invention wherein R, $R_1$ and/or $R_2$ are methoxy or ethoxy may be dealkylated, such as heretofore described in connection with reaction schemes I and II, and are therefore useful as intermediates in the preparation of the corresponding hydroxy compounds.

The foregoing may be better understood in connection with the following examples:

EXAMPLE 1

1-aminomethyl-4,5-methylenedioxy-phthalan HCl 0.0154 moles of 1-aminomethyl-4,5-methylenedioxy-phthalide HCl is suspended in 10 ml. of dry tetrahydrofuran (THF) in a 250 ml. 3-neck round bottom flask equipped with a magnetic stirrer and reflux condenser, under a nitrogen atmosphere. Over a period of 15 minutes, 0.117 moles of 1M diborane in THF is added to the reaction mixture. The reaction mixture is refluxed overnight, then cooled in an ice bath. Methanolic hydrochloric acid is added to the reaction mixture and the mixture is stirred for 1½ hours to decompose excess diborane. The mixture is then evaporated and treated with 3 volumes of methanol, followed by evaporation, to remove any excess hydrochloric acid and/or residual diborane complex. The crude residue is crystallized from ethanol/ether to yield 1-aminomethyl-4,5-methylenedioxy-phthalan HCl as a white solid, m.p. 203°–204° C.

EXAMPLE 2

1-isopropylaminomethyl-4,5-methylenedioxy-phthalan HCl

The procedure of Example 1 is repeated using 1-isopropylaminomethyl-4,5-methylenedioxy-phthalide HCl as the starting material to obtain 1-isopropylaminomethyl-4,5-methylenedioxy-phthalan HCl as a white solid, m.p. 249°–250° C.

EXAMPLE 3

1-dimethylaminomethyl-4,5-methylenedioxy-phthalan HCl

The procedure of Example 1 is repeated using 1-dimethylaminomethyl-4,5-methylenedioxy-phthalide HCl as the starting material to obtain 1-dimethylaminomethyl-4,5-methylenedioxy-phthalan HCl as a white solid, m.p. 220°–221° C.

EXAMPLE 4

1-di-n-proylaminomethyl-4,5-methylenedioxy-phthalan HCl

The procedure of Example 1 is repeated using 1-di-n-propylaminomethyl-4,5-methylenedioxy-phthalide HCl as the starting material to obtain 1-di-n-propylaminomethyl-4,5-methylenedioxy-phthalan HCl as a white solid, m.p. 170°–171° C.

EXAMPLE 5

1-p-methoxyphenyl-3-butylaminomethyl-4,5-methylenedioxy-phthalan HCl

The procedure of Example 1 is repeated using 1-p-methoxyphenyl-3-butyl]aminomethyl-4,5-methylenedioxyphthalide HCl as the starting material to obtain 1-p-methoxyphenyl-3-butylaminomethyl-4,5-methylenedioxy-phthalan HCl as a white solid, m.p. 185°–187° C.

EXAMPLE 6

1-aminomethyl-4,5-dihydroxy-phthalan HBr 0.0061 moles of 1-aminomethyl-4,5-methylenedioxyphthalan HCl is suspended in 35 mls. of dry methylene chloride, and then cooled to −78° C. in a dry ice/acetone bath. To this mixture is added dropwise, 0.0234 moles of boron tribromide in 10 ml. of methylene chloride over a period of 15 minutes. The reaction mixture is stirred under a nitrogen atmosphere at −78° C. for 3 hours. Methanol (25 ml) is added to the reaction mixture and stirred for a period of 0.5 hours at 0° C. to decompose excess boron tribromide. The reaction mixture is then warmed to room temperature for an additional 2 hours. The mixture is then evaporated and the residue recrystallized from ethanol/ether to obtain 1-aminomethyl-4,5-dihydroxy-phthalan HBr as a solid, m.p. 218°–220° C.

EXAMPLE 7

1-isopropylaminomethyl-4,5-dihydroxy-phthalan HBr

The procedure of Example 6 is repeated using 1-isopropylaminomehyl-4,5-methylenedioxy-phthalan HCl as the starting material to obtain 1-isopropylaminomethyl-4,5-dihydroxy-phthalan HBr as a white solid, m.p. 185°–186° C.

EXAMPLE 8

1-dimethylaminomethyl-4,5-dihydroxy-phthalan HBr

The procedure of Example 6 is repeated using 1-dimethylaminomethyl-4,5-methylenedioxy-phthalan HCl as the starting material, to obtain 1-dimethylaminomethyl-4,5-dihydroxy-phthalan HBr as a white solid, m.p. 190°–192° C.

EXAMPLE 9

1-di-n-proylaminomethyl-4,5-dihydroxy-phthalan HBr

The procedure of Example 6 is repeated using 1-di-n-propylaminomethyl-4,5-methylenedioxy-phthalan HCl as the starting material to obtain 1-di-n-propylaminomethyl-4,5-dihydroxy-phthalan HBr as a white solid, m.p. 105°–107° C.

EXAMPLE 10

1-aminomethyl-5,6-dimethoxy-phthalan HCl

The procedure of Example 1 is repeated using 1-aminomethyl-5,6-dimethoxy-phthalide HCl as the starting material to obtain 1-aminomethyl-5,6-dimethoxy-phthalan HCl.

EXAMPLE 11

1-isopropylaminomethyl-5,6-dimethoxy-phthalan HCl

The procedure of Example 1 is repeated using 1-isopropylaminomethyl-5,6-dimethoxy-phthalide HCl as the starting material to obtain 1-isopropylaminomethyl-5,6-dimethoxy-phthalan HCl.

EXAMPLE 12

1-dimethylaminomethyl-5,6-dimethoxy-phthalan HCl

The procedure of Example 1 is repeated using 1-dimethylaminomethyl-5,6-dimethoxy-phthalide HCl as the starting material to obtain 1-dimethylaminomethyl-5,6-dimethoxy-phthalan HCl as a white solid, m.p. 225°–226° C.

EXAMPLE 13

1-di-n-proylaminomethyl-5,6-dimethoxy-phthalan HCl

The procedure of Example 1 is repeated using 1-di-n-propylaminomethyl-5,6-dimethoxy-phthalide HCl as the starting material to obtain 1-di-n-propylaminomethyl-5,6-dimethoxy-phthalan HCl as a white solid, m.p. 191°–192° C.

EXAMPLE 14

1-aminomethyl-5,6-dihydroxy-phthalan HBr

To 0.0127 mole of 1-aminomethyl-5,6-dihydroxyphthalide HBr suspended in 55 ml. of dry THF is added dropwise 0.0956 moles of 1M diborane in THF over a period of 15 minutes. The reaction mixture is refluxed for 21 hours. Excess diborane is decomposed with freshly prepared methanolic hydrobromic acid, the mixture is stirred for a period of 3 hours, and then evaporated to dryness. The residue is recrystallized from methanol/ether to obtain 1-aminomethyl-5,6-dihydroxy-phthalan HBr as a white solid, m.p. 237°–238° C.

EXAMPLE 15

1-isopropylaminomethyl-5,6-dihydroxy-phthalan HBr

The procedure of Example 14 is repeated using 1-isopropylaminomethyl-5,6-dihydroxy-phthalide HCl as the starting material to obtain 1-isopropylaminomethyl-5,6-dihydroxy-phthalan HBr as a white solid, m.p. 176°–177° C.

EXAMPLE 16

1-dimethylaminomethyl-5,6-dihydroxy-phthalan HBr

The procedure of Example 14 is repeated using 1-dimethylaminomethyl-5,6-dihydroxy-phthalide HCl as the starting material to obtain 1-dimethylaminomethyl-5,6-dihydroxy-phthalan HBr as a white solid, m.p. 224°–225° C.

EXAMPLE 17

1-di-n-propylaminomethyl-5,6-dihydroxy-phthalan HBr

The procedure of Example 14 is repeated using 1-di-n-propylaminomethyl-5,6-dihydroxy-phthalide HCl as the starting material to obtain 1-di-n-propylaminomethyl-5,6-dihydroxy-phthalan HBr as a white solid, m.p. 211°–212° C.

EXAMPLE 18

1-aminomethyl-4,6-dimethoxy-phthalan HCl

The procedure of Example 14 is repeated using 1-aminomethyl-4,6-dimethoxy-phthalide HCl as the starting material and refluxing the methanolic hydrobromic acid with methanolic hydrochloric acid to obtain 1-aminomethyl-4,6-dimethoxy-phthalan HCl as a white solid, m.p. 218°–220° C.

EXAMPLE 19

1-isopropylaminomethyl-4,6-dimethoxy-phthalan HCl

The procedure of Example 18 is repeated using 1-isopropylaminomethyl-4,6-dimethoxy-phthalide HCl as the starting material to obtain 1-isopropylaminomethyl-4,6-dimethoxy-phthalan HCl as a white solid, m.p. 210°–213° C.

EXAMPLE 20

1-dimethylaminomethyl-4,6-dimethoxy-phthalan HCl

The procedure of Example 18 is repeated using 1-dimethylaminomethyl-4,6-dimethoxy-phthalide HCl as the starting material to obtain 1-dimethylaminomethyl-4,6-dimethoxy-phthalan HCl as a white solid, m.p. 220°–221° C.

EXAMPLE 21

1-di-n-propylaminomethyl-4,6-dimethoxy-phthalan HBr

The procedure of Example 14 is repeated using 1-di-n-propylaminomethyl-4,6-dimethoxy-phthalide HCl as a starting material to obtain 1-di-n-propylaminomethyl-4,6-dimethoxy-phthalan HBr.

EXAMPLE 22

1-aminomethyl-4,6-dihydroxy-phthalan HBr

The procedure of Example 6 is repeated using 1-aminomethyl-4,6-dimethoxy-phthalan HCl as the starting material to obtain 1-aminomethyl-4,6-dihydroxy-phthalan HBr.

EXAMPLE 23

1-isopropylaminomethyl-4,6-dihydroxy-phthalan HBr

The procedure of Example 6 is repeated using 1-isopropylaminomethyl-4,6-dimethoxy-phthalan HCl as the starting material to obtain 1-isopropylaminomethyl-4,6-dihydroxy-phthalan HBr.

EXAMPLE 24

1-dimethylaminomethyl-4,6-dihydroxy-phthalan HBr

The procedure of Example 6 is repeated using 1-dimethylaminomethyl-4,6-dimethoxy-phthalan HCl as the starting material to obtain 1-dimethylaminomethyl-4,6-dihydroxy-phthalan HBr.

EXAMPLE 25

1-di-n-propylaminomethyl-4,6-dihydroxy-phthalan HBr

The procedure of Example 6 is repeated using 1-di-n-propylaminomethyl-4,6-dimethoxy-phthalan HCl as the starting material to obtain 1-di-n-propylaminomethyl-4,6-dihydroxy-phthalan HBr.

EXAMPLE 26

1-benzodioxanemethylaminomethyl-4,5-methylenedioxy-phthalan HCl 1-aminomethyl-4,5-methylenedioxy-phthalan HCl is heated overnight with 2-hydroxymethylbenzodioxane-p-toluene sulfonate and diisopropylethylamine to yield 1-benzodioxanemethylaminomethyl-4,5-methylenedioxyphthalan HCl.

EXAMPLE 27

1-[2(4-chloro-2,6-dimethoxyphenoxy)-ethyl]-aminomethyl-4,5-methylenedioxy-phthalan HCl 1-aminomethyl-4,5-methylenedioxy-phthalan HCl is reacted with the acid chloride of 4-chloro-2,6-dimethoxyphenoxy acetic acid, and then treated with diborane to obtain 1-[2(4-chloro-2,6-dimethoxyphenoxy)-ethyl]-aminomethyl-4,5-methylenedioxy-phthalan HCl.

EXAMPLE 28

1-[1-(3,4-dimethoxyphenyl)-2-ethyl]-aminomethyl-4,5-methylenedioxy-phthalan HCl 1-aminomethyl-4,5-methylenedoxy-phthalan HCl is reacted with the acid chloride of 3,4-dimethoxyphenyl acetic acid, and then with diborane to obtain 1-[1-(3,4-dimethoxyphenyl)-2-ethyl]-aminomethyl-4,5-methylenedioxy-phthalan HCl.

EXAMPLE 29

1-[2-(2-methoxyphenoxy)-ethyl]-aminomethyl-4,5-methylenedioxy-phthalan HCl 1-aminomethyl-4,5-methylenedioxy-phthalan HCl is reacted with the acid chloride of 2-methoxyphenoxy acetic acid, and then with diborane to obtain 1-[2-(2-methoxyphenoxy)-ethyl]-aminomethyl-4,5-methylenedioxy-phthalan HCl.

EXAMPLE 30

1-[1-(3-chloro-4-methoxyphenyl)-3-butyl]-aminomethyl-4,5-methylenedioxy-phthalan HCl The procedure of Example 5 is repeated using 1-[1-(3-chloro-4-methoxyphenyl)-3-butyl]-aminomethyl-4,5-methylenedioxy-phthalide HCl as the starting material to obtain 1-[1-(3-chloro-4-methoxyphenyl)-3-butyl]-aminomethyl-4,5-methylenedioxy-phthalan HCl.

EXAMPLE 31

1-[1-phenyl-2-propyl]-aminomethyl-4,5-methylenedioxy-phthalan HCl

The procedure of Example 5 is repeated using 1-[1-phenyl-2-propyl]-aminomethyl-4,5-methylenedioxy-phthalide HCl as the starting material to obtain 1-[1-phenyl-2-propyl]-aminomethyl-4,5-methylenedioxy-phthalan HCl.

EXAMPLE 32

1-[1-p-chlorophenyl-2-propyl]-aminomethyl-4,5-methylenedioxy-phthalan HCl

The procedure of Example 5 is repeated using 1-[1-p-chlorophenyl-2-propyl]-aminomethyl-4,5-methylenedioxy-phthalide HCl as the starting material to obtain 1-[1-p-chlorophenyl-2-propyl]-aminomethyl-4,5-methylenedioxy-phthalan HCl.

EXAMPLE 33

1-[1-(3,4-methylenedioxy-phenyl)-2-propyl]-aminomethyl-4,5-methylenedioxy-phthalan HCl The procedure of Example 5 is repeated using 1-[1-(3,4-methylenedioxy-phenyl)-2-propyl]-aminomethyl-4,5-methylenedioxy-phthalide HCl as the starting material to obtain 1-[1-(3,4-methylenedioxy-phenyl)-2-propyl]-aminomethyl-4,5-methylenedioxy-phthalan HCl.

EXAMPLE 34

1-[1-(3,4-dimethoxy-phenyl)-2-propyl]-aminomethyl-4,5-methylenedioxy-phthalan HCl The procedure of Example 5 is repeated using 1-[1-(3,4-dimethoxy-phenyl)-2-propyl]-aminomethyl-4,5-methylenedioxy-phthalide HCl as the starting material to obtain 1-[1-(3,4-dimethoxy-phenyl)-2-propyl]-aminomethyl-4,5-methylenedioxy-phthalan HCl.

EXAMPLE 35

1-benzylaminomethyl-4,5-methylenedioxy-phthalan HCl

The procedure of Example 5 is repeated using 1-benzylaminomethyl-4,5-methylenedioxy-phthalide HCl as the starting material to obtain 1-benzylaminomethyl-4,5-methylenedioxy-phthalan HCl.

EXAMPLE 36

1-aminomethyl-5-methoxy-6-chloro-phthalan.HCl

The procedure of Example 1 is repeated using 1-aminomethyl-5-methoxy-6-chloro-phthalide.HCl as the starting material to obtain 1-aminomethyl-5-methoxy-6-chloro-phthalan.HCl.

EXAMPLE 37

1-[1-phenyl-2-propyl]-aminomethyl-4,5-dihydroxy-phthalan.HCl

The procedure of Example 6 is repeated using 1-[1-phenyl-2-propyl]-aminomethyl-4,5-methylenedioxy-phthalan HCl as the starting material to obtain 1-[1-phenyl-2-propyl]-aminomethyl-4,5-dihydroxy-phthalan HCl.

EXAMPLE 38

1-[1-(3,4-dihydroxy-phenyl)-2-propyl]-aminomethyl-4,5-dihydroxy-phthalan HCl

The procedure of Example 6 is repeated using 1-[1-(3,4-methylenedioxy-phenyl)-2-propyl]-aminomethyl-4,5-methylenedioxy-phthalan HCl as the starting material to obtain 1-[1-(3,4-dihydroxy-phenyl)-2-propyl]-aminomethyl-4,5-dihydroxy-phthalan HCl.

EXAMPLE 39

1-aminomethyl-4-methoxy-phthalan HCl

The procedure of Example 1 is repeated using 1-aminomethyl-4-methoxy-phthalide HCl as the starting material to obtain 1-aminomethyl-4-methoxy-phthalan HCl.

EXAMPLE 40

1-aminomethyl-4-hydroxy-phthalan HBr

The procedure of Example 6 is repeated using 1-aminomethyl-4-methoxy-phthalan HCl as the starting material to obtain 1-aminomethyl-4-hydroxy-phthalan HBr.

EXAMPLE 41

1-aminomethyl-5-methoxy-phthalan HCl

The procedure of Example 1 is repeated using 1-aminomethyl-5-methoxy-phthalide HCl as the starting material to obtain 1-aminomethyl-5-methoxy-phthalan HCl.

EXAMPLE 42

1-aminomethyl-5-hydroxy-phthalan HBr

The procedure of Example 6 is repeated using 1-aminomethyl-5-methoxy-phthalan HCl as the starting material to obtain 1-aminomethyl-5-hydroxy-phthalan HBr.

EXAMPLE 43

1-aminomethyl-6-methoxy-phthalan HCl

The procedure of Example 1 is repeated using 1-aminomethyl-6-methoxy-phthalide HCl as the starting material to obtain 1-aminomethyl-6-methoxy-phthalan HCl.

EXAMPLE 44

1-aminomethyl-6-hydroxy-phthalan HBr

The procedure of Example 6 is repeated using 1-aminomethyl-6-methoxy-phthalan HCl as the starting material to obtain 1-aminomethyl-6-hydroxy-phthalan HBr.

EXAMPLE 45

1-aminomethyl-7-methoxy-phthalan HCl

The procedure of Example 1 is repeated using 1-aminomethyl-7-methoxy-phthalide HCl as the starting material to obtain 1-aminomethyl-7-methoxy-phthalan HCl.

EXAMPLE 46

1-aminomethyl-7-hydroxy-phthalan HBr

The procedure of Example 6 is repeated using 1-aminomethyl-7-methoxy-phthalan HCl as the starting material to obtain 1-aminomethyl-7-hydroxy-phthalan HBr.

The therapeutic activity of the compounds can be demonstrated in vivo by their ability to decrease arterial blood pressure and/or heart rate in the spontaneously hypertensive rat as follows. A group of Okamoto rats, which develop hypertension spontaneously when reaching young adulthood, are deprived of food for a period of 16 hours and are placed in semi-restraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically, cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pulses reappear during deflation at approximately the same pressure, and aterial blood pressure is thereby established by cuff pressure at the point of pulse appearance. The heart rate is determined from the arterial pulse wave. A 100 mg./kg. dose of a test compound of formula I is administered orally to each rat of the test group, and five interference-free signals are recorded on a Model 7 Grass polygraph for each rat at various measurement periods following administration. By following the foregoing procedure, the tested preferred compounds of the invention are shown to decrease the arterial blood pressure and/or heart rate of rats of the group.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg. of active ingredient per kg. of body weight per day are administered orally to a mammalian patient suffering from hypertension. If desired, the daily dose may be divided into multiple doses for administration, e.g., two to four separate doses per day.

What is claimed is:

1. A compound of the formula

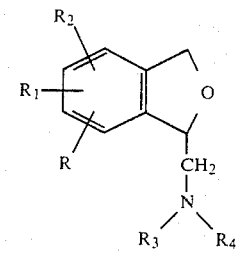

wherein R, $R_1$, and $R_2$ are independently selected from hydrogen, hydroxy, thiomethyl, or

wherein $R_5$ and $R_6$ are independently selected from hydrogen, loweracyl of 1 to 4 carbon atoms or sulfonyl of the formula

wherein $R_7$ is loweralkyl of 1 to 4 carbon atoms; and wherein no more than one of R, $R_1$ or $R_2$ is hydrogen; and $R_3$ and $R_4$ are independently selected from hydrogen; loweralkyl of 1 to 4 carbon atoms; or halo-substituted loweralkyl of 1 to 4 carbon atoms; and the pharmaceutically acceptable salts thereof.

2. A compound of claim 1 wherein one of R, $R_1$, and $R_2$ is hydrogen and the remaining two of R, $R_1$ and $R_2$ are hydroxy.

3. A compound of claim 1 wherein $R_3$ and $R_4$ are hydrogen.

4. A compound of claim 1 wherein $R_3$ is isopropyl and $R_4$ is hydrogen.

5. A compound of claim 1 wherein $R_3$ and $R_4$ are methyl.

6. A compound of claim 1 wherein R, $R_3$ and $R_4$ are hydrogen, and $R_1$ and $R_2$ are hydroxy, namely 1-aminomethyl-4,5-dihydroxy-phthalan.

7. A composition in pharmaceutical dosage form for the treatment of hypertension comprising an anti-hypertensive effective amount of a compound of the formula

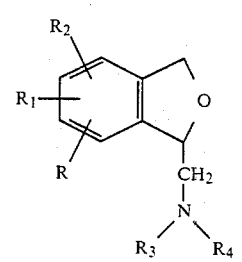

wherein R, R₁, and R₂ are independently selected from hydrogen, hydroxy, thiomethyl, or

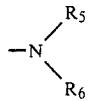

wherein R₅ and R₆ are independently selected from hydrogen, loweracyl of 1 to 4 carbon atoms or sulfonyl of the formula

wherein $R_7$ is loweralkyl of 1 to 4 carbon atoms; and wherein no more than one of R, R₁, or R₂ is hydrogen; and R₃ and R₄ are independently selected from hydrogen; loweralkyl of 1 to 4 carbon atoms; or halo-substituted loweralkyl of 1 to 4 carbon atoms; and the pharmaceutically acceptable salts thereof and a pharmaceutically acceptable carrier or diluent.

* * * * *